(12) United States Patent
Wu

(10) Patent No.: US 7,284,414 B2
(45) Date of Patent: Oct. 23, 2007

(54) HARDNESS TESTING DEVICE

(76) Inventor: Shaoming Wu, 1846 Red Robin Pl., Thousand Oaks, CA (US) 91320

( * ) Notice: Subject to any disclaimer, the term of this patent is extended or adjusted under 35 U.S.C. 154(b) by 162 days.

(21) Appl. No.: 11/015,712

(22) Filed: Dec. 16, 2004

(65) Prior Publication Data
US 2006/0130566 A1    Jun. 22, 2006

(51) Int. Cl.
*G01N 3/52* (2006.01)
(52) U.S. Cl. .......................................................... 73/79
(58) Field of Classification Search .................... 73/79, 73/12.09, 12.11, 12.13
See application file for complete search history.

(56) References Cited

U.S. PATENT DOCUMENTS

| | | | | |
|---|---|---|---|---|
| 1,586,363 | A * | 5/1926 | Hall | 73/79 |
| 3,576,127 | A * | 4/1971 | Weitzel et al. | 73/79 |
| 4,034,603 | A * | 7/1977 | Leeb et al. | 73/79 |
| 4,411,153 | A * | 10/1983 | Lewis | 73/79 |
| 5,197,473 | A * | 3/1993 | Fedorov et al. | 600/398 |
| 5,959,198 | A * | 9/1999 | Pollok et al. | 73/79 |
| 6,354,148 | B2 * | 3/2002 | Sato et al. | 73/79 |

* cited by examiner

*Primary Examiner*—Robert Raevis
(74) *Attorney, Agent, or Firm*—Raymond Y. Chan; David and Raymond Patent Group

(57) ABSTRACT

A hardness testing device includes an elongated guiding tube, a test member, an impact actuator, and a transducer. The elongated guiding member has a bottom impact opening for contacting with the work piece surface and a coil seat integrally provided on an outer circumferential surface of the guiding tube at a position close to the impact opening. The impact actuator is provided on an upper portion of the guiding tube for applying an impact force against the test member which is then driven to travel within the guiding tube at an impinging velocity and a rebound velocity. The transducer includes an electric coil coaxially wound on the coil seat, and is adapted to electromagnetically communicate with the test member for detecting the impinging velocity and the rebound velocity when the test member slidably passes through the coil seat so as to determine a hardness of the work piece surface.

10 Claims, 7 Drawing Sheets

HARDNESS TESTING DEVICE

BACKGROUND OF THE PRESENT INVENTION

1. Field of Invention

The present invention relates to hardness testing, and more particularly to a hardness testing device comprising an electric coil coaxially and integrally wounded on a guiding tube so as to minimize a clearance between a test member and the electric coil for achieving more accurate hardness testing results.

2. Description of Related Arts

Hardness testing is extremely important for mechanical engineers. An accurate testing result effectively assists mechanical engineers in selecting appropriate materials and making an optimal engineering design in a wide variety of circumstances.

As a matter of conventional arts, there exists various hardness testing devices in which they can be broadly categorized as either handheld type or stationary type. One particular handheld type hardness testing device measures hardness of work pieces by Leeb Hardness Value wherein a test member, which is usually embodied as a predetermined type of magnetic materials, is driven to impinge against a work piece surface at a predetermined impact velocity. When the test member rebounds from the work piece surface, the impact velocity and a rebound velocity are recoded and interpreted according to a particular scientific formula and other engineering tolerances to come up with a Leeb Hardness Value.

Thus, a conventional hardness testing device of this type, as shown in FIG. 1 of the drawings, usually comprises a supporting tube 10P having an test opening 11P formed at a bottom thereof, a test member 20P moving along the supporting tube 10P, an actuation device provided on the supporting tube 10P and adapted to drive the test member 20P to impinge on the work piece surface so as to develop the impact velocity and the rebound velocity, and a hardness transducer 40P comprising a coil assembly 41P and a data processor. The coil assembly 41P is usually mounted on the supporting tube 10P at a position near the testing opening 11P and loaded with an electric current for producing a magnetic field inside the supporting tube at the portion surrounded by the coil assembly 41P. The data processor is electrically connected with the coil assembly 41P in such a manner that when the test member passes through the magnetic field at the impact velocity and the rebound velocity, the magnetic field would be interfered to an extent that the impact velocity and the rebound velocity can be determined by the data processor in accordance with conventional established scientific formulas. Moreover, once the impact velocity and the rebound velocity have been determined, the hardness of the work piece surface can also be determined as, for example, a Leeb Hardness Value (HL), by the following equation:

$$HL = (\text{Rebound velocity}/\text{Impact Velocity}) \times 1000$$

A major drawback for this type of conventional hardness testing device is that the essence of the hardness testing depends on the impact velocity and the rebound velocity of the test member, which is driven by the actuation device. It follows that the manner of which the test member 20P hits the work piece surface is of crucial importance in developing the impact velocity and the rebound velocity. For example, the impinge angle of the test member directly affects the distance by which the test member 20P travels in the magnetic field so as to affect an accurate detection of the relevant velocities (the impact velocity and the rebound velocity). Therefore, it is expected that the greater the clearance between the test member 20P and the coil assembly 41P, the greater the error in detecting the relevant velocities. The reason is that according to simple electromagnetic theory, the smaller the clearance between the test member 20P and the coil assembly 41P, the stronger the electric current induced in the coil 411P and therefore, the higher the measurement accuracy.

From this it is suggested that for the above-mentioned conventional hardness testing device, there usually exists a substantial clearance between the coil assembly 41P and the corresponding test member 20P. This clearance is expected to account for substantial measurements error during conventional hardness measurements. The reason for the existence of this substantial clearance is that the conventional coil assembly 41P usually comprises a holder 43P mounted to the supporting tube 10P while the coil 411P is wound on this holder. As a result, due to the physical dimension of this holder 43P, a substantial clearance between the coil 411P and the test member 20P is inevitably expected.

SUMMARY OF THE PRESENT INVENTION

A main object of the present invention is to provide a hardness testing device which is capable of accurately measuring a surface hardness of a work piece based on the Leeb principle, i.e. determination of the surface hardness by the respective velocity of a test member before and after impinging on the work piece.

Another object of the present invention is to provide a hardness testing device comprising an electric coil coaxially and integrally wounded on a guiding tube so as to minimize a clearance between a test member and the electric coil for achieving more accurate hardness testing results.

Another object of the present invention is to provide a hardness testing device comprising an angle sensor for detecting a working angle of the hardness testing device so as to adjust the surface hardness in light of any inclination of the hardness testing device. In other words, the present invention is adapted for being utilized in a wide variety of circumstances.

Another object of the present invention is to provide a hardness testing device which does not involve any holder for mounting the electric coil, so that the guiding tube is smaller in size for use in confined environments.

Another object of the present invention is to provide a hardness testing device which is simple in structure, easy to use, and suitable for use to detect the surface hardness of a wide variety of materials.

In order to accomplish the above objects, the present invention provides a hard testing device, comprising for measuring a hardness of a work piece surface, comprising:

an elongated guiding tube having a bottom impact opening for contacting with the work piece surface and a coil seat integrally provided on an outer circumferential surface of the guiding tube at a position close to the impact opening;

a test member slidably moving within the guiding tube;

an impact actuator provided on an upper portion of the guiding tube for applying an impact force against the test member such that the test member travels within the guiding tube at an impinging velocity before impacting with the work piece surface and at a rebound velocity after impacting with the work piece surface; and a transducer, which comprises:

an electric coil coaxially wound on the coil seat to minimize a clearance between the electric coil and the test member when the test member slidably passes through the coil seat, wherein the electric coil is adapted to electromagnetically communicate with the test member for detecting the impinging velocity and the rebound velocity of the test member when the test member slidably passing through the coil seat; and a hardness interpreter electrically connected with the electric coil for measuring a hardness of the work piece surface with respect to the impinging velocity and the rebound velocity.

These and other objectives, features, and advantages of the present invention will become apparent from the following detailed description, the accompanying drawings, and the appended claims.

DETAILED DESCRIPTION OF THE PREFERRED EMBODIMENT

Figure 1:
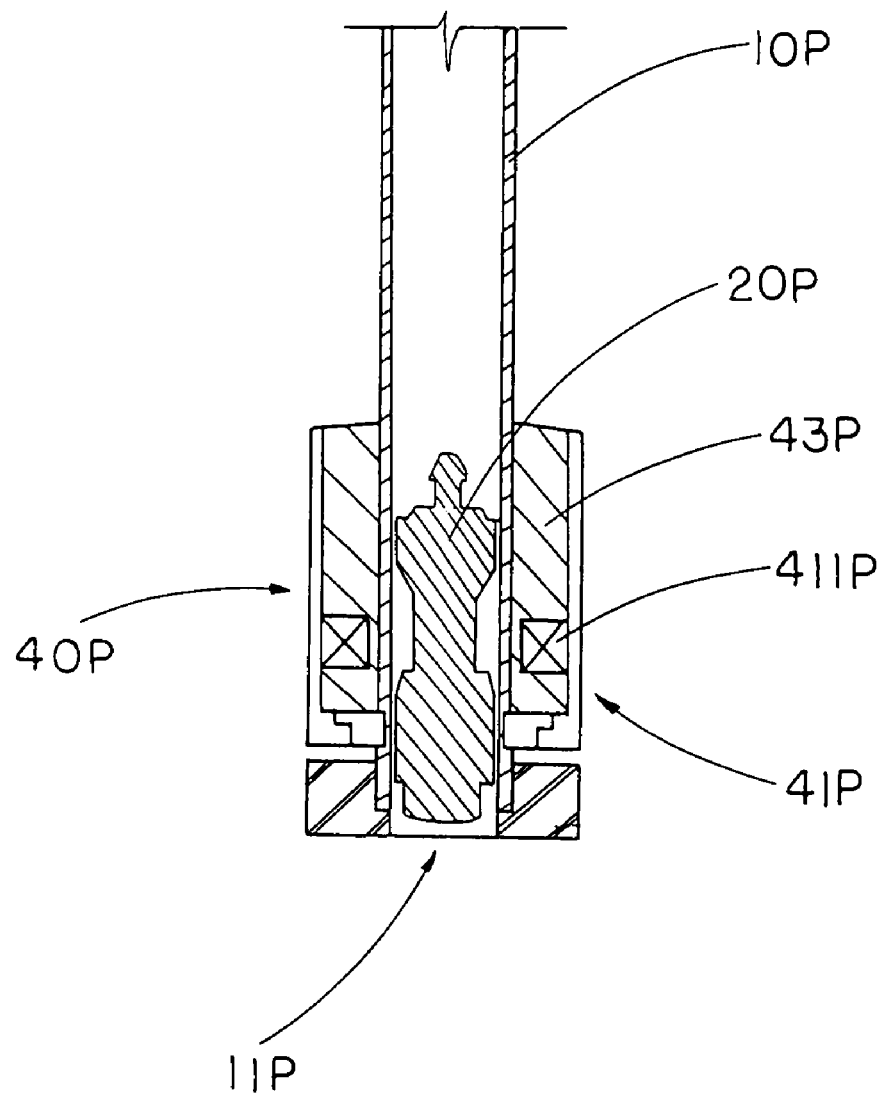
FIG. 1 is a conventional hardness testing device.
Figure 2:
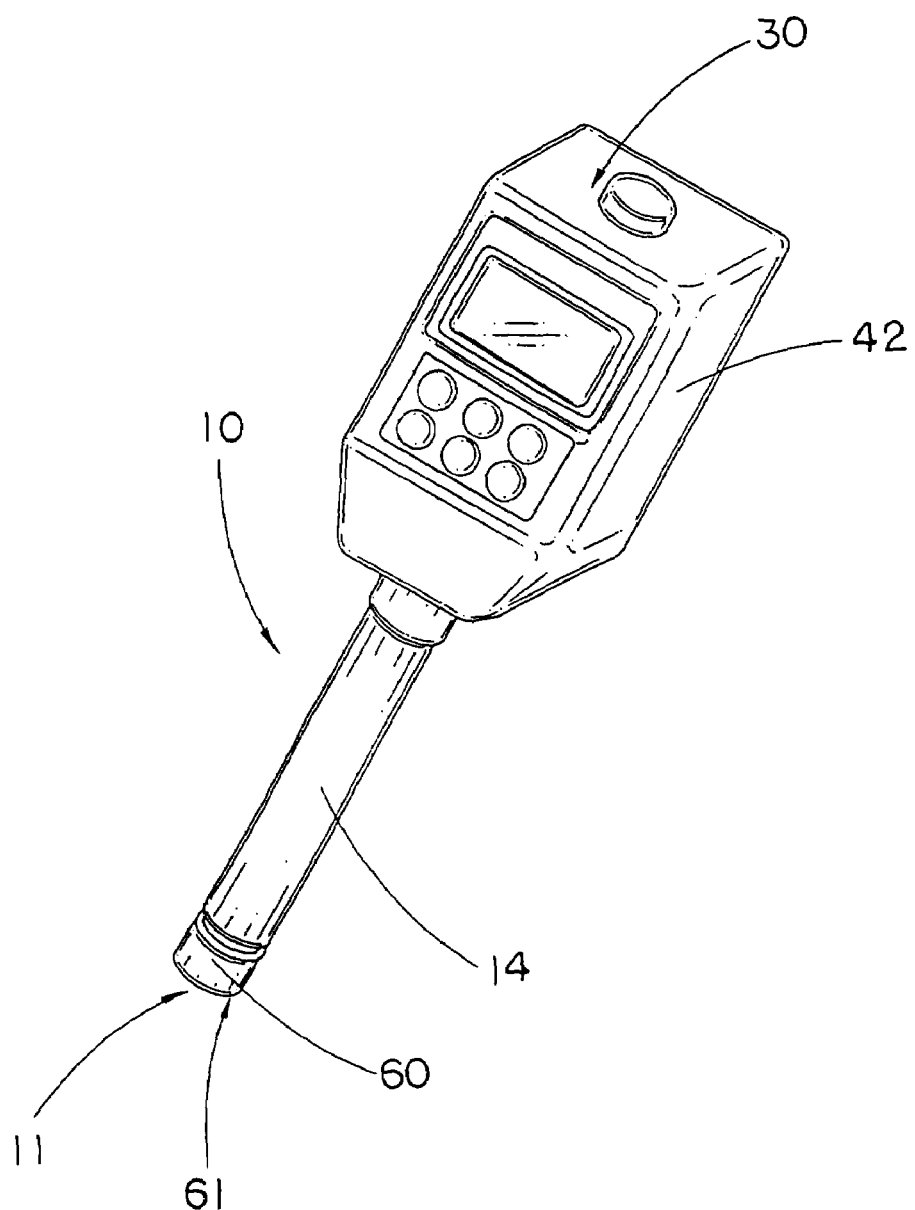
FIG. 2 is a perspective view of a hardness testing device according to a preferred embodiment of the present invention.
Figure 3:
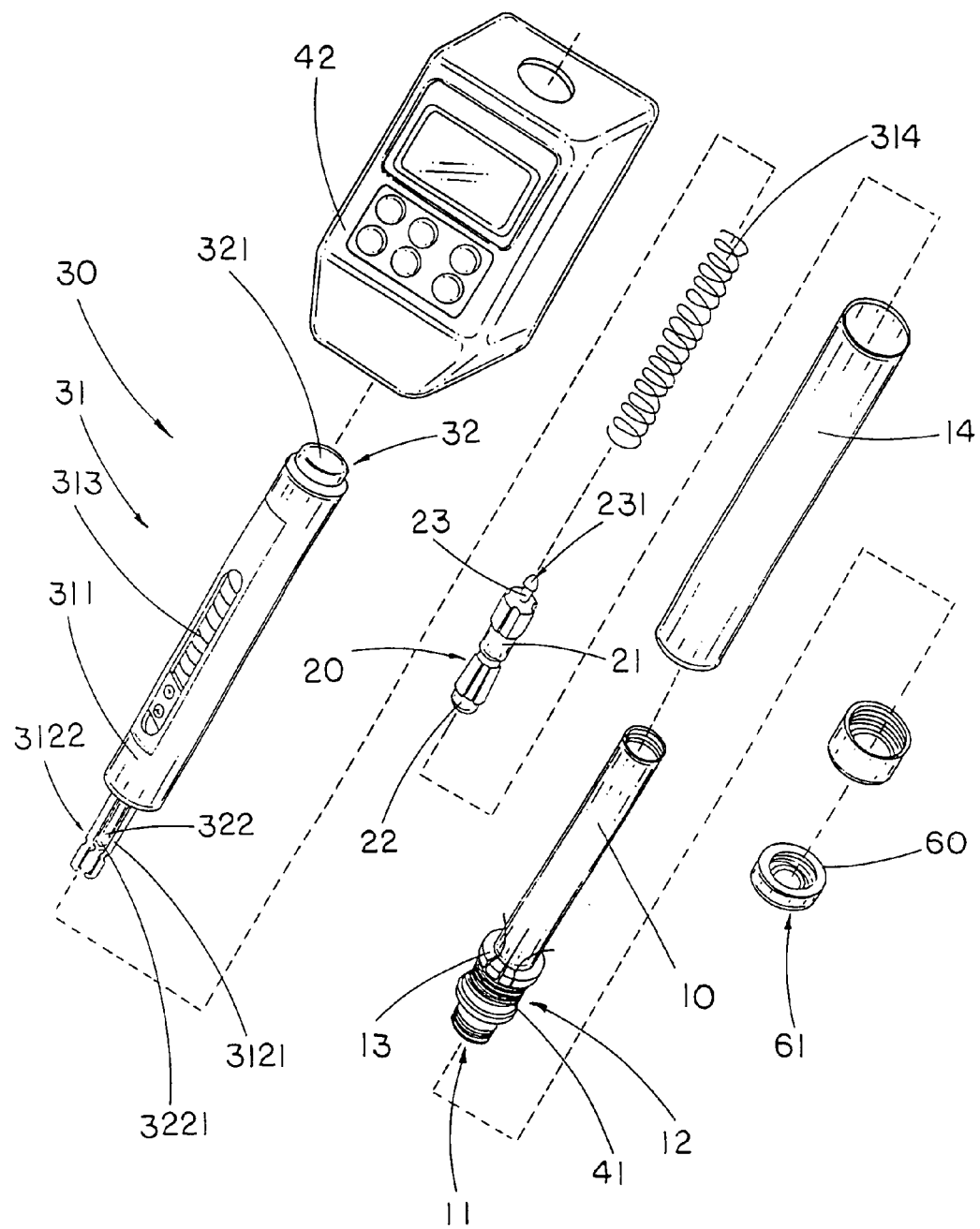
FIG. 3 is an exploded perspective view of the hardness testing device according to the above preferred embodiment of the present invention.
Figure 5:
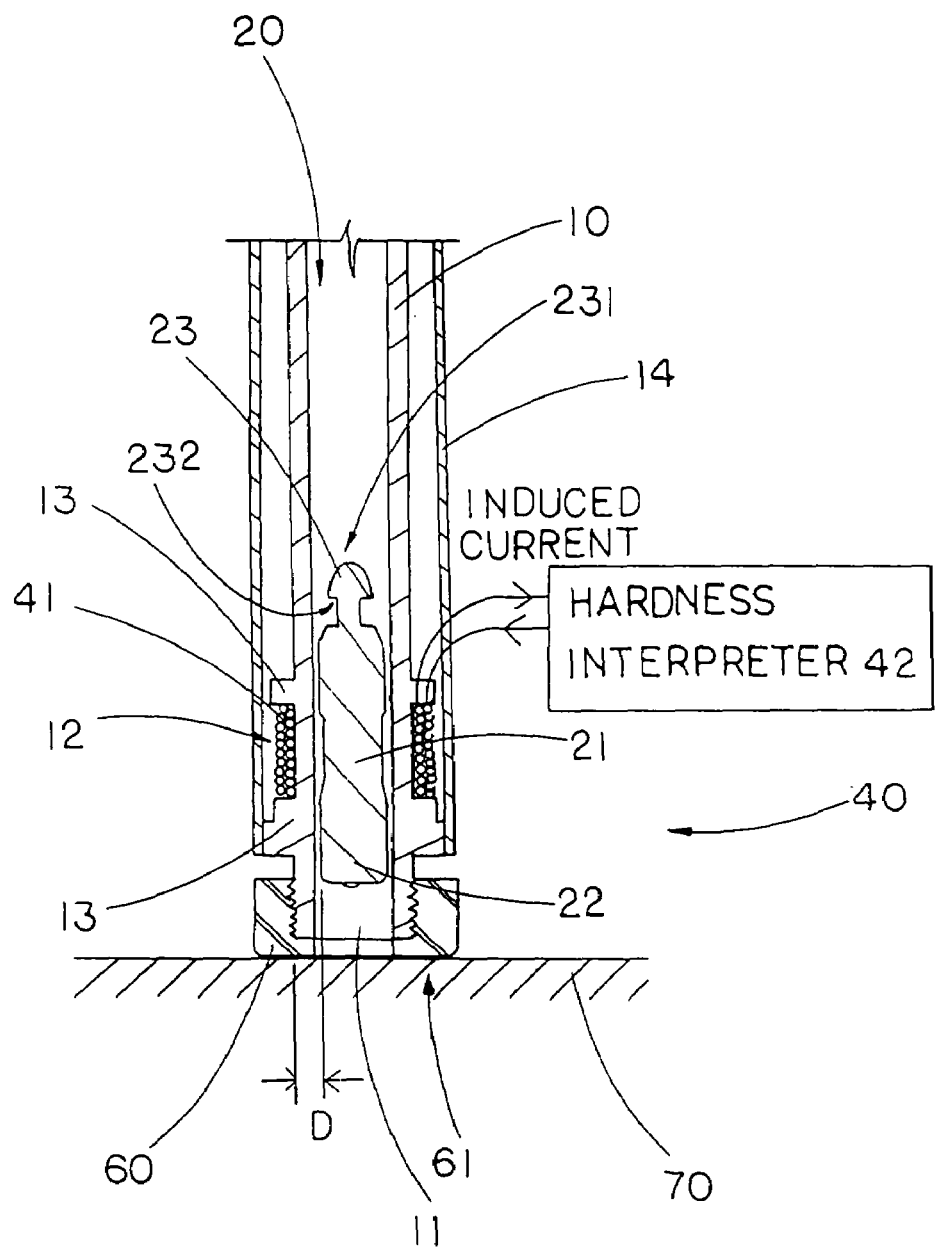
FIG. 5 is schematic diagram illustrating that the test member induces an electric current to the electric coil, while the electric current is interpreted by the hardness interpreter.

Referring to FIG. 2, FIG. 3, and FIG. 5 of the drawings, a hardness testing device for measuring a hardness of a work piece surface 70 is illustrated, in which the hardness testing device comprises a hardness test guider, which is embodied as an elongated guiding tube 10, a test member 20 slidably moving within the guiding tube 10, an impact actuator 30, and a transducer 40.

The elongated guiding tube 10 has a bottom impact opening 11 for contacting with the work piece surface 70, and a coil seat 12 integrally provided on an outer circumferential surface of the guiding tube 10 at a position close to the impact opening 11 thereof.

The impact actuator 30 is provided on an upper portion of the guiding tube 10 for applying an impact force against the test member 20 such that the test member 20 is driven to travel within the guiding tube 10 at an impinging velocity before impacting with the work piece surface 70, and at a rebound velocity after impacting with the work piece surface 70, wherein any difference between the impinging velocity and the rebound velocity is subject to the hardness of the work piece surface 70, as well as energy loss during the impact.

The transducer 40 comprises an electric coil 41 and a hardness interpreter 42. The electric coil 41 is coaxially wound on the coil seat 12 to minimize a clearance D between the electric coil 41 and the test member 20 when the test member 20 slidably passes through the coil seat 12, wherein the electric coil 41 is electromagnetically communicated with the test member 20 for detecting the impinging velocity and the rebound velocity of the test member 20 when the test member 20 slidably passing through the coil seat 12.

On the other hand, a hardness interpreter 42 is electrically connected with the electric coil 41 for measuring the hardness of the work piece surface 70 with respect to the impinging velocity and the rebound velocity. Accordingly, the hardness interpreter 42 is mounted at the impact actuator 30 so as to allow slim structure of the guiding tube 10 at the coil seat 12.

In other words, the electric coil 41 is retained on the outer circumferential surface of the guiding tube 10 at the coil seat 12 to electrically connect to the hardness interpreter 42.

In order to protect the coil seat 12, the hardness testing device further comprises an outer covering tube 14 wherein the guiding tube 10 and the impact actuator 30 are disposed within the outer covering tube 14. Since the hardness interpreter 42 is electrically connected at the impact actuator 30, and the coil seat 12 is integrally formed on the guiding tube 10, the guiding tube 10 and a lower portion of the outer covering tube 14 by which the coil seat 12 is covered is allowed to be crafted and designed to form a slim structure such that a user is able to place the lower portion of the outer covering tube 14 in confined areas for the purpose of hardness testing.

Referring to FIG. 2 to FIG. 3 of the drawings, the guiding tube 10 further has two spaced apart holding rings 13 coaxially, outwardly and integrally extended from the circumferential surface of the guiding tube 10 to form the coil seat 12 between the two holding rings 13, wherein the electric coil 41 is integrally and coaxially wound on the coil seat 12 between the two holding rings 13 for generating an electric current corresponding with the impinging velocity and the rebound velocity when the test member 20 passes through the coil seat 12 at the impinging velocity and the rebound velocity respectively.

One of the holding rings 13 has two guiding slits 131 spacedly and transversely formed thereon, wherein two end portions of the electric coil 41 are extended from the coil seat 12 to the hardness interpreter 42 through the guiding slits 131 respectively such that the two end portions of the electric coil 41 are retained on the outer circumferential surface of the guiding tube 10 at the guiding slits 131 respectively to electrically connect to the hardness interpreter 42.

It is worth mentioning that by integrally and coaxially winding the electric coil 41 on the coil seat 12, when the test member 20 passes through the coil seat 12, the test member 20 is capable of producing a uniform electromagnetic field within the coil seat 12 for inducing the electric current corresponding with the relevant velocity of the test member 20.

It is also worth pointing out that since the electric coil 41 is wound on the coil seat 12 which is the circumferential surface of the guiding tube 10, the clearance D can be minimized to ensure minimum error in measuring the impinging velocity and the rebound velocity of the test member 20. Accordingly, the test member 20 has a size slightly smaller than a diameter of the guiding tube 10 such that the test member 20 is fittingly and coaxially sliding along the guiding tube 10 to impinge on the work piece surface so as to enhance the measures of the impinging velocity and the rebound velocity of the test member 20.

The test member 20 comprises a magnetic body 21 and an impact head 22 integrally provided at a bottom tip of the magnetic body 21 for impinging with the work piece surface 70 at the impinging velocity. The magnetic body 21 is preferably made of magnetic materials such as regular magnet, so that when it passes through the seat coil 12, it would electromagnetically communicate with the electric coil 41 to create the relevant electric current corresponding to the velocity of the test member 20, wherein the electric current is fed into the hardness interpreter 42 for measurement of the velocity of the test member 20 and the corresponding surface hardness of the work piece surface 70.

On the other hand, the impact head 22 is preferably made of diamond or tungsten-carbide having a predetermined hardness for impinging on the work piece surface 70. The impact head 22 is preferably spherical in shape so as to ensure a single contact point between the impact head 22 and the work piece surface 70 for minimizing energy loss during impact and evenly distributing the impact force to the entire impact head 22.

Moreover, the test member 20 further comprises an engaging connector 23 upwardly extended from the magnetic body 21 for detachably engaging with the impact actuator 30 so as to be driven thereby to impinge on the work piece surface 70 at the impinging velocity.

Figure 4A:
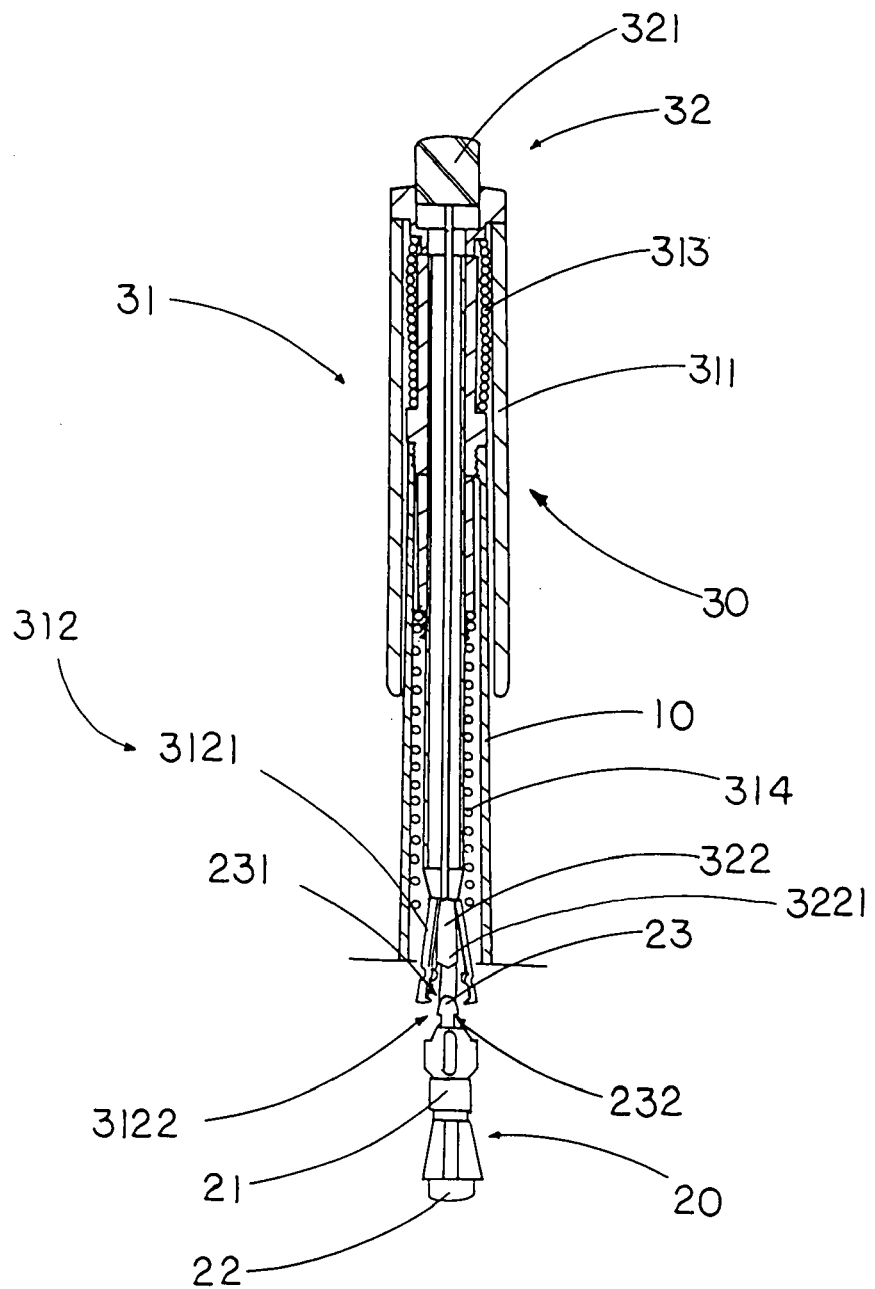
FIG. 4A and FIG. 4B are schematic diagrams illustrating that the loading holder are at the loading position and the release position respectively.
Figure 4B:
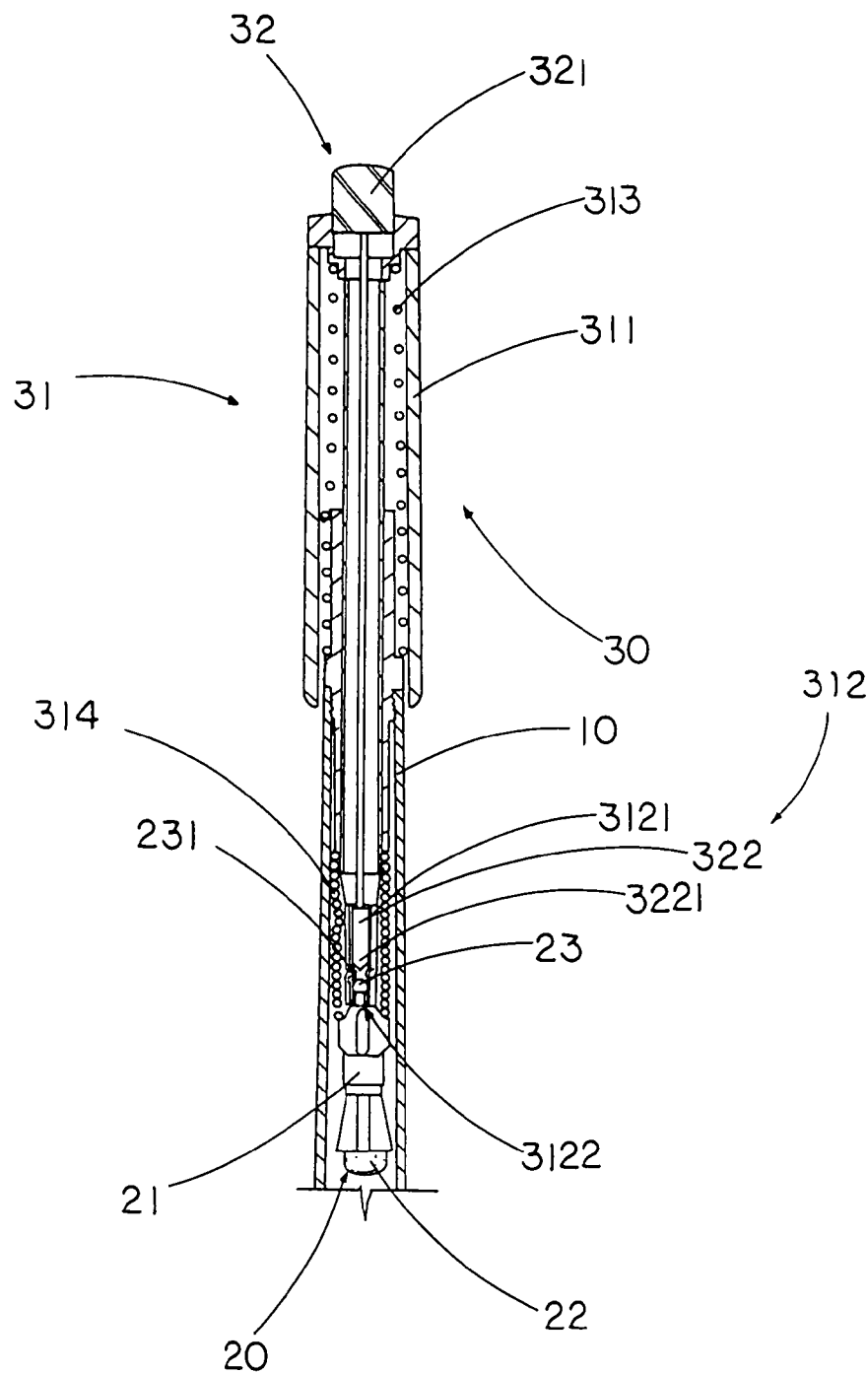

As shown in FIG. 3, FIG. 4A and FIG. 4B of the drawings, the impact actuator 30 comprises an actuation piston 31 supported by the guiding tube 10 for detachably engaging with the engaging connector 23 of the test member 20, and a manual release controller 32 operatively provided on the actuation piston 31 for selectively disengaging the engaging connector 23 from the actuation piston 31 so as to release the test member 20 traveling towards the work piece surface 70.

Moreover, the actuation piston 31 comprises a tubular supporting member 311 mounted on the guiding tube 10 and a loading holder 312 slidably extended in the tubular supporting member 311 for moving between a loading position and a release position, wherein at the loading position, the loading holder 312 is downwardly and slidably depressed along the tubular supporting member to engage with the engaging connector 23 of the test member 20, and at the release position, the loading holder 312, having engaged with the engaging connector 23, is upwardly and slidably moved along the tubular supporting member 311 for upwardly pulling the test member 20 elevated along the guiding tube 10 so as to be selectively released by the manual release controller 32 to impinge the work piece surface 70 at the impinging velocity.

Moreover, the loading holder 312 further comprises at least two gripping arms 3121 slidably extended towards the test member 20. Accordingly, there are three gripping arms 3121 movably and integrally extended from a bottom end portion thereof, in which each of the three gripping arms 3121 has a free end potion slightly and inwardly bent to form a gripping hook 3122 for engaging with the engaging connector 23 of the test member 20.

Accordingly, the engaging connector 23 has an enlarged and outwardly inclined top guiding portion 231 to define an engaging shoulder 232 thereon in such a manner that when the loading holder 312 is slid within the guiding tube 10 from the release position to the loading position, the three gripping arms 3121 are arranged to be guided and slightly pushed from the loading holder 312 by the top guiding portion 231 until the three gripping hooks 3122 are depressed to engage with the engaging shoulder 232. The test member 20 is loaded to the actuation piston 31 when the gripping hooks 3122 are getting closer to each other as the gripping arms 3121 are drawn into the guiding tube 10.

According to the preferred embodiment of the present invention, the actuation piston 31 further comprises a resilient element 313 mounted on the tubular supporting member 311 to normally apply an upward urging force as an upward pulling force for normally retaining the loading holder 312 at the release position. In other words, once the loading holder 312 is slid within the supporting member 311 by manual to the extent that the gripping hooks 3121 have been engaged with the engaging shoulder 232 of the engaging connector 23, the resilient element 313 is arranged to pull the loading holder 3122 upwardly so as to suspendedly elevate the test member 20 ready for being driven to impinge the work piece surface 70.

The manual release controller 32 comprises a pusher button 321 movably mounted at the top end of the guiding tube 10, and a pusher pin 322 having an actuation end connected with the pusher button 321, and a pusher end 3221 extended along the loading holder 312 to communicate with the three gripping arms 3121 in such a manner that when the pusher button 321 is depressed, the pusher pin 322 is driven to depressed so that the pusher end 3221 of the pusher pin 322 is also depressed to slightly and outwardly push the three gripping arms 3121 to such an extent to disengage the gripping hooks 3122 with the engaging shoulder 232 of the engaging connector 23. In other words, the pusher end 3221 of the pusher pin 322 is downwardly moved to push the gripping arm 3121 at a position that the three gripping arms 3121 are moving away each other to release the engaging connector 23. Then, the test member 20 is allowed to fall along the guiding tube 10 for impinging on the work piece surface 70.

In order to control the impinging velocity of the test member 20, the impact actuator 30 further comprises a resilient member 314 mounted on the tubular supporting member 311 for normally applying an downward urging force for pushing the test member 20. In other words, when the loading holder 312 is slid within the supporting member 311 to load the engaging connector 23, the resilient member 314 is being compressed at the same time. As a result, when the pusher button 321 is depressed to disengage the three gripping hooks 3122 from the engaging shoulder 232, in addition to gravitational force, the test member 20 is pushed via the compressed resilient member 314 to impinge on the work piece surface 70 at the impinging velocity through the impact opening 11 of the guiding tube 10.

Accordingly, the resilient member 314 is a compression spring disposed in the guiding tube 10 for applying a spring loading force as the downward urging force against the test member 20. The loading holder 312 is slidably disposed in the guiding tube 10 to detachably hold the test member 20 when the spring loading force of the resilient member 314 is loaded such that when the test member 20 is released to disengage with the loading holder 312, the test member 20 is slidably pushed via the compressed resilient member 314 towards the impact opening 11 at the impinging velocity by the spring loading force. In other words, when the loading holder 312 is pushed towards the impact opening 11 to substantially engage the gripping hooks 3122 of the gripping arms 3121 with the test member 20, the resilient member 314 is loaded with the spring loading force so as to slidably elevate the test member 20 away from the impact opening 11.

Referring to FIG. 2, FIG. 3 and FIG. 5 of the drawings, the electric coil 41 is embodied as being made up from regular conductive wire wound on the outer circumferential surface of the guiding tube 10 at the coil seat 12, and electrically connected with the hardness interpreter 42.

When the test member 20 passes through the coil seat 12 as released from the impact actuator 30, the magnetic field carried thereby would induce a current to the electric coil 41 the strength of which is corresponding with the velocity of the test member 20. The electric current thus induced would then pass the hardness interpreter 42 which is adapted for calculating the corresponding impinging velocity of the test member 20 with respective to the electric current.

Once the test member 20 has hit the work piece surface 70, it is rebounded with the rebound velocity with respective to the surface hardness of the work piece surface 70. Once again, when the test member 20 passes through the coil seat 12 at the rebound velocity, the magnetic field carried by the test member 20 will induce a current to the electric coil 41 wherein the strength of that current is corresponding with the rebound velocity. The electric current thus induced would then pass the hardness interpreter 42 which is adapted for calculating the corresponding rebound velocity of the test member 20 with respective to the electric current.

According to the preferred embodiment, the hardness interpreter 42 is programmed to calculate from the impinging velocity and the rebound velocity into Leeb Hardness Value (HL), by the following equation:

$$HL = (\text{Rebound velocity}/\text{Impact Velocity}) \times 1000$$

Figure 6:
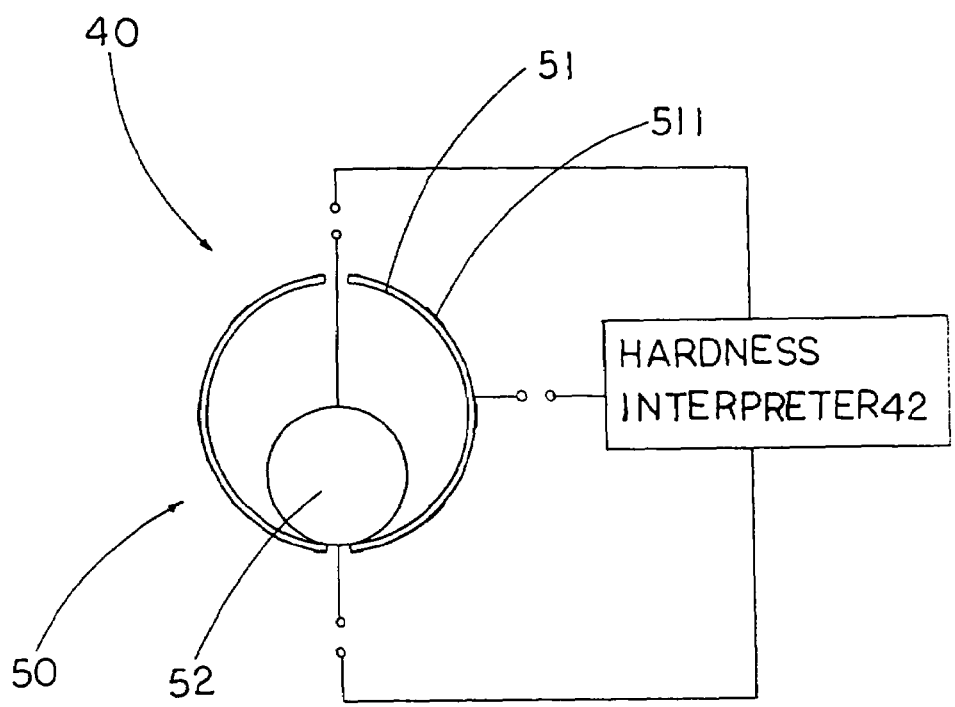
FIG. 6 is a schematic diagram of the operation of the angle sensor according to the above preferred embodiment of the present invention.

Referring to FIG. 2, FIG. 3 and FIG. 6 of the drawings, in order to enhance the accuracy and the range of operation of the present invention, the hardness testing device further comprises an angle sensor 50 electrically incorporated with the transducer 40 to measure an operation angle of the present invention, and to perform an appropriate adjustment to the surface hardness of the work piece surface 70 to take into account of any inclination of the hardness testing device.

According to the preferred embodiment, the angle sensor 50 comprises an insulating holder 51, having a plurality of electrodes 511 spacedly formed at an outer side thereof to represent a predetermined operation angle of the hardness testing device, and provided in the hardness interpret 42, and an angle indicator 52 movably supported within the insulating holder 51 in such a manner that it is capable of electrically contacting any one of the electrodes in the insulating holder 51 to generate a sensor signal for indicating a respective operation angle of the hardness testing device. Accordingly, when the bottom impact opening 11 of the guiding tube 10 is contacted with the work piece surface 70, the angle indicator 52 is correspondingly moved within the insulating holder 51 so as to measure the angle of the work piece surface 70. If the work piece surface 70 is a horizontal surface, the angle indicator 52 is moved at a center of the insulating holder 51. If the work piece surface 70 is a slanted surface, the angle indicator 52 is moved towards one of the electrodes 511. Therefore, by determining the location of the angle indicator 52 within the insulating holder 51, the angle of the work piece surface 70 will be measured. The sensor signal is then fed into the hardness interpreter 42 for adjusting a surface hardness calculation so as to produce an accurate result with respect to the work piece surface 70 and the operation angle of the hardness testing device. In other words, when the guiding tube 10 is inclinedly supported on the work piece surface, the angle indicator 52, which is embodied as a metal ball, is moved within the insulating holder 51 to electrically contact with one of the electrodes 511 with respect to the inclination of the guiding tube 10 so as to determine the operation angle thereof for adjustment. It is worth to mention that the insulating holder 51, having a ball shape, is made of insulating material such as plastic to prevent the angle indicator 52 electrically contacting with the insulating holder 51. In addition, two electric wires are extended into the insulating holder 51 to electrically connect with the angle indicator 52.

Referring to FIG. 2 to FIG. 3 of the drawings, in order to ensure uniformity of what is essentially a manual measurement process, the hardness testing device further comprises an alignment head 60, having an alignment surface 61, provided at the bottom impact opening 11 of the elongated guiding tube 10 for aligning the alignment surface 61 with the work piece surface 70 when the hardness testing device is actuated to measure the surface hardness of the work piece surface 70.

From the forgoing descriptions, it can be shown that the above mentioned objects have been substantially achieved. The present invention provides a hardness testing device which minimizes a clearance between the test member 20 and the electric coil 41 so as to produce a more precise and accurate result for measuring the surface hardness of the work piece surface 70.

Moreover, the present invention is equipped with an angle sensor 50 for allowing adjustment of result in light of an operation angle, such as inclination, of the hardness testing device. The operation angle is liable to interfere with the impinging velocity and the rebound velocity of the test member, therefore, an adjustment taking into account of the operation angle would produce an even more accurate surface hardness reading of the relevant work piece.

Finally, as mentioned above, since the electric coil 41 is integrally wound on the guiding tube 10, an overall size thereof and the outer covering tube 14 can be minimized as compared with conventional hardness testing device due to the presence of the coil holder. It is also worth mentioning that the present invention may be electrically connected to a printing device for instantaneously printing out the measurement data.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A hardness testing device for measuring a hardness of a work piece surface, comprising:

an elongated guiding tube having a bottom impact opening for contacting with said work piece surface and a coil seat formed on an outer circumferential surface of said guiding tube at a position close to said impact opening, wherein said coil seat has two spaced apart guiding slits;

a test member slidably moving within said guiding tube;

an impact actuator provided on an upper portion of said guiding tube for applying a force against said test member such that said test member travels within said guiding tube at an impinging velocity before impacting with said work piece surface and at a rebound velocity after impacting with said work piece surface; and a transducer, which comprises:

an electric coil coaxially wound on said coil seat to minimize a clearance between said electric coil and said test member when said test member slidably passes through said coil seat is adapted to electromagnetically communicate with said test member for detecting said impinging velocity and said rebound velocity of said test member when said test member is slidably passing through said coil seat; and a hardness interpreter arranged for measuring a hardness of said work piece surface with respect to said impinging velocity and said rebound velocity, wherein two end portions of said electric coil are extended from said coil seat to said upper portion of said guiding tube along said outer circumferential surface thereof to electrically connect to said hardness interpreter through said guiding slits respectively so as to retain said two end portion of said electric coil on said outer circumferential surface of said guiding tube.

2. The hardness testing device, as recited in claim 1, wherein said guiding tube further has two spaced apart holding rings coaxially, outwardly and integrally extended from said outer circumferential surface of said guiding tube to define said coil seat on said outer circumferential surface of said guiding tube between said two holding rings, wherein said electric coil is coaxially wound on said coil seat between said two holding rings for generating an electric current corresponding with said impinging velocity and said rebound velocity when said test member passes through said coil seat at said impinging velocity and said rebound velocity respectively.

3. The hardness testing device, as recited in claim 2, wherein said two guiding slits are spacedly formed at one of said holding rings such that said two end portions of said electric coil are extended from said coil seat to said hardness interpreter through said guiding slits respectively along said outer circumferential surface of said guiding tube to electrically connect to said hardness interpreter.

4. The hardness testing device, as recited in claim 3, wherein said test member comprises a magnetic body and an impact head integrally provided at a bottom tip of said magnetic body for impinging with said work piece surface at said impinging velocity, wherein said magnetic body is made of magnetic materials so that when said test member passes through said coil seat, said magnetic body is adapted to electromagnetically communicate with said electric coil to produce said corresponding electric current to be measured by said hardness interpreter.

5. The hardness testing device, as recited in claim 4, wherein said impact head is made of tungsten-carbide having a predetermined hardness for impinging on said work piece surface, and is spherical in shape so as to ensure a single contact point between said impact head and said work piece surface for minimizing an energy loss during an impact between said impact head and said work piece surface for achieving an accurate hardness testing result.

6. The hardness testing device, as recited in claim 1, wherein said test member comprises a magnetic body and an impact head integrally provided at a bottom tip of said magnetic body for impinging with said work piece surface at said impinging velocity, wherein said magnetic body is made of magnetic materials so that when said test member passes through said coil seat, said magnetic body electromagnetically communicates with said electric coil to produce said corresponding electric current to be measured by said hardness interpreter.

7. The hardness testing device, as recited in claim 6, wherein said impact head is made of tungsten-carbide having a predetermined hardness for impinging on said work piece surface, and is spherical in shape so as to ensure a single contact point between said impact head and said work piece surface for minimizing an energy loss during an impact between said impact head and said work piece surface for achieving an accurate hardness testing result.

8. A hardness test guider for a hardness testing device comprising a test member adapted for slidably moving within said hardness test guider at an impinging velocity and a rebound velocity, and a hardness interpreter which comprises an electric coil of a transducer for being induced a predetermined electrical current corresponding with said impinging velocity and said rebound velocity, wherein said hardness test guider comprises:

an elongated guiding tube having a bottom impact opening for contacting with a work piece surface, wherein said test member is allowed to slidably move along said guiding tube to impinge on said work piece surface at said impinging velocity and rebound at said rebound velocity; and a coil seat provided on an outer circumferential surface of said guiding tube for supporting said electric coil of said transducer at a position close to said impact opening, wherein said coil seat has two spaced apart guiding slits for two end portions of said electric coil extending from said coil seat to said hardness interpreter along said outer circumferential surface of said guiding tube;

thereby, when said test member slidably passes through said coil seat at said impinging velocity and rebounds at said rebound velocity in said guiding tube, said electric current is induced at said electric coil for detecting said hardness of said work piece surface.

9. The hardness test guider, as recited in claim 8, further having two spaced apart holding rings coaxially, outwardly and integrally extended from said outer circumferential surface of said guiding tube to form said coil seat between said two holding rings, wherein said two holding rings are adapted for retaining said electric coil at a position that said electric coil is coaxially wound on said coil seat between said two holding rings for generating an electric current corresponding with said impinging velocity and said rebound velocity when said test member passes through said coil seat at said impinging velocity and said rebound velocity respectively.

10. The hardness test guider, as recited in claim 9, wherein said two guiding slits are spacedly formed at one of said holding rings for said two end portions of said electric coil extending from said coil seat to said hardness interpreter through said guiding slits respectively along said outer circumferential surface of said guiding tube.

* * * * *